United States Patent [19]

Shinohara et al.

[11] 4,421,756
[45] Dec. 20, 1983

[54] QUINOLINONEIMINE CARBOXYLIC ACID ANTI-INFLAMMATORY AND ANALGESIC COMPOSITION CONTAINING THE COMPOUND

[75] Inventors: Tatsuo Shinohara; Yukihiro Oguri; Yukio Fujimori; Hiroyuki Kondo, all of Toyama, Japan

[73] Assignee: Daito Koeki Kabushiki Kaisha, Toyama, Japan

[21] Appl. No.: 296,262

[22] PCT Filed: Oct. 9, 1980

[86] PCT No.: PCT/JP80/00243
§ 371 Date: Aug. 18, 1981
§ 102(e) Date: Aug. 18, 1981

[87] PCT Pub. No.: WO81/01001
PCT Pub. Date: Apr. 16, 1981

[30] Foreign Application Priority Data

Oct. 12, 1979 [JP] Japan ............... 54-132105

[51] Int. Cl.³ ............. A61K 31/47; C07D 215/54
[52] U.S. Cl. ................. 424/258; 546/159; 562/456
[58] Field of Search ............ 546/159; 424/258

[56] References Cited

U.S. PATENT DOCUMENTS

| | | | |
|---|---|---|---|
| 3,542,785 | 11/1970 | Carney | 424/258 X |
| 4,044,134 | 8/1977 | Althuis et al. | 546/159 X |
| 4,221,797 | 9/1980 | Hardtmann et al. | 424/258 |

FOREIGN PATENT DOCUMENTS

| | | | |
|---|---|---|---|
| 55-85547 | 6/1980 | Japan . | |
| 55-85568 | 6/1980 | Japan | 546/159 |
| WO81/1001 | 4/1981 | PCT Int'l Appl. . | |

OTHER PUBLICATIONS

Nagai, et al., Chemical Abstracts, vol. 70, 67824k (1969).

Primary Examiner—Diana G. Rivers
Attorney, Agent, or Firm—Parkhurst & Oliff

[57] ABSTRACT

This invention concerns a novel compound represented by the general formula (I), a process for producing the novel compound of the formula (I) by reacting the compound of the formula (II) with the compound of the formula (III), as well as an anti-inflammatory and analgesic composition containing the compound of the formula (I):

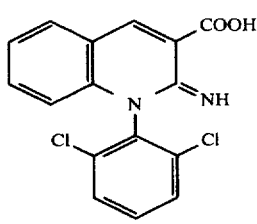

Formula (I)

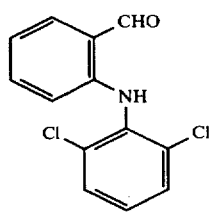

Formula (II)

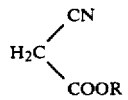

Formula (III)

(R represents hydrogen or lower alkyl group).

2 Claims, 3 Drawing Figures

COMPOUND OF FORMULA (I) ACCORDING TO THIS INVENTION 50mg/kg p.o.

2 % CARRAGEENIN 0.1ml/site

QUINOLINONEIMINE CARBOXYLIC ACID ANTI-INFLAMMATORY AND ANALGESIC COMPOSITION CONTAINING THE COMPOUND

TECHNICAL FIELD

This invention concerns a novel compound, a production process therefor and an anti-inflammatory and analgesic composition containing the novel compound.

DISCLOSURE OF INVENTION

This invention concerns 1-(2,6-dichlorophenyl)-2-quinolinoneimine-3-carboxylic acid represented by the general formula:

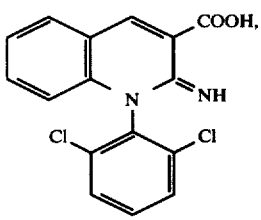

(I)

a process for producing the same and an anti-inflammatory and analgesic composition containing the novel compound.

The compound of the formula (I) according to this invention can be obtained at high yield by reacting N-(2,6-dichlorophenyl)-anthranylaldehyde represented by the formula

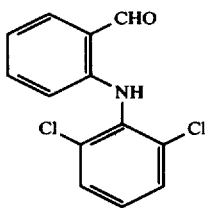

(II)

with cyanoacetic acid or its ester represented by the general formula

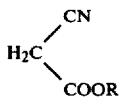

(III)

wherein R represents hydrogen or lower alkyl group, in particular, methyl, ethyl, propyl or butyl group, then treating with an alkali.

The compound of the formula (I) according to this invention can provide, in admixture with known carrier(s), an anti-inflammatory and analgesic composition showing excellent effects.

BEST MODE FOR CARRYING OUT THE INVENTION

Figure 1:
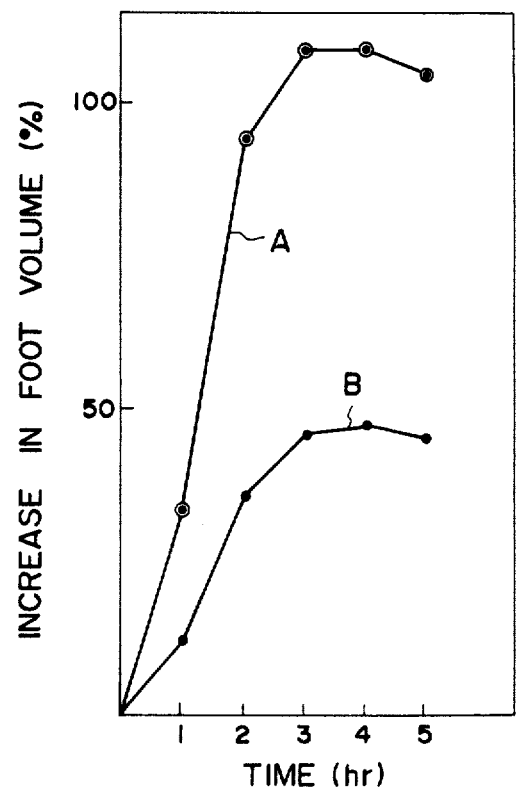
FIG. 1 is a graph showing the result of an edema test using the compound of formula (I) according to this invention.

The process for producing the compound of the formula (I) according to this invention is explained below by way of a flow diagram.

The route A is explained in detail at first.

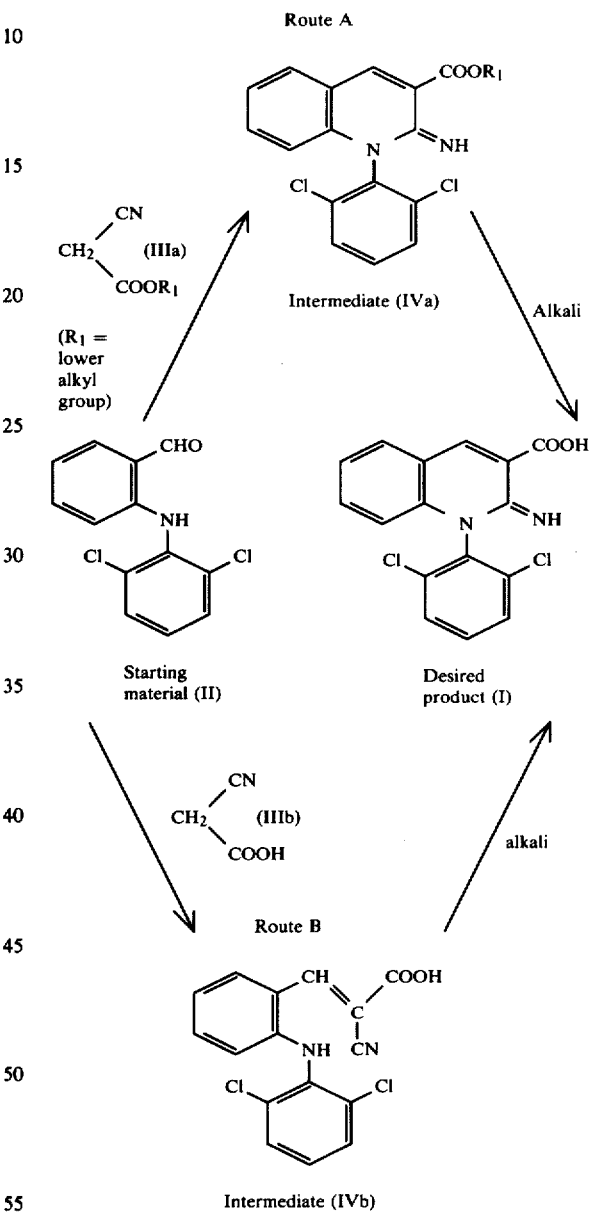

An intermediate 1-(2,6-dichlorophenyl)-3-alkoxycarbonyl-2-quinolinoneimine of the formula (IVa) is obtained through the condensing reaction of N-(2,6-dichlorophenyl)anthranylaldehyde of the formula (II) with a cyanoacetic ester of the formula (IIIa). In the reaction, the compound of the formula (IIIa) is preferably used in 1–3 mol, particularly 1.1–2.0 mol, per one mol of the compound of the formula (II). The catalyst used herein includes a mixture of organic acid salt and acetic acid, for example a mixture of ammonium acetate and acetic acid, a mixture of piperidium acetate and acetic acid, or a mixture of piperidium benzoate and acetic acid, use of the mixture of ammonium acetate and acetic acid being particularly preferred. For the amount of the catalyst, ammonium acetate is used in 0.5–5 mol, preferably 1.0–2.0 mol, and acetic acid is used in 0.5–10 mol, preferably 1.0–4.0 mol, per one mol of the compound of the formula (II). Any solvents inert to the reaction such as benzene, toluene, or xylene may be used, with particular preference being given to the use of such solvents capable of facilitating the reaction while eliminating water resulting from the condensation as azeotropic mixture. The reaction time is about 1–12 hour, preferably about 2–5 hours. The reaction temperature is preferably near the boiling point of the solvent employed.

1-(2,6-dichlorophenyl)-2-quinolinoneimine-3-carboxylic acid (I) which is the desired compound according to this invention can be obtained by hydrolyzing the intermediate (IVa) thus obtained using an alkali. The alkali used in the hydrolyzing reaction may include, for example, alkali metal hydroxide such as potassium hydroxide and sodium hydroxide, alkaline earth metal hydroxide such as calcium hydroxide and barium hydroxide, alkali metal carbonate such as sodium carbonate, and alkali metal hydrogen carbonate such as sodium hydrogen carbonate. Use of the alkali metal hydroxide, especially, potassium hydroxide and sodium hydroxide, is particularly preferred. The amount used is 1–5 mol, preferably 1.2–2 mol per one mol of the compound of the formula (IVa). Any solvents inert to the reaction can be used and they include, for example, methanol, ethanol, propanol, dimethylformamide and dimethylsulfoxide, use of methanol or ethanol being preferred among all. The reaction time is about 1–12 hours, preferably about 2–6 hours. The reaction temperature is about 30°–150° C., preferably about 60°–80° C.

The route B is to be detailed next.

An intermediate 2-cyano-3-[2-(2,6-dichloroanilino)-phenyl]acrylic acid of the formula (IVb) can be obtained by reacting the compound of the formula (II) with the cyano-acetic acid of the formula (IIIb). In the reaction, the compound of the formula (IIIb) is preferably used in 1–3 mol, preferably 1.1–2.0 mol, per one mol of the compound of the formula (II). The reaction conditions such as the type and the amount of the catalyst, the type and the amount of the solvent, the reaction time and the reaction temperature are determined also in this case in the same manner as the conditions for the condensing reaction between the compound of the formula (II) and the compound of the formula (IIIA) in the route A referred to above.

1-(2,6-dichlorophenyl)-2-quinolinoneimine-3-carboxylic acid (I) which is the desired compound according to this invention can be obtained by treating the compound of the formula (IVb) thus obtained using an alkali. The reaction conditions such as the type and the amount of the alkali, the type of the solvent, the reaction time and the reaction temperature are determined in the same manner as the conditions for the alkali hydrolyzing reaction to the compound of the formula (IVa) in the route A referred to above.

The 1-(2,6-dichlorophenyl)-2-quinolinoneimine-3-carboxylic acid (I) as the desired compound according to this invention thus obtained and its pharmacologically acceptable salts exhibit anti-inflammatory and analgesic actions. Accordingly, the 1-(2,6-dichlorophenyl)-2-quinolinoneimine-3-carboxylic acid (I) and pharmacologically acceptable salts thereof may be formulated, in admixture with known carriers, into appropriate pharmaceutical formulations, for example, tablets, capsules, powders, suspensions, syrups, ointments, granules, injections and suppositories for oral, non-oral or local administration.

The compound of the formula (I) according to this invention is useful also as an intermediate material for the production of known o-(2,6-dichloroanilino)phenyl acetic acid exhibiting anti-inflammatory, analgesic and anti-pyretic actions.

The best mode of this invention is to be described by way of preferred examples in more detail.

EXAMPLE 1

Preparation of
1-(2,6-dichlorophenyl)-3-ethoxycarbonyl-2-quinolinoneimine

A mixture of 150 g of N-(2,6-dichlorophenyl)-anthranylaldehyde, 98 g of cyanoethyl acetate, 128 g of acetic acid, 78 g of ammonium acetate and 750 ml of benzene was refluxed in a reaction vessel equipped with a water content removing device for three hours while removing water. After being allowed to cool, the reaction solution was washed with water and the water-washed phase was separated. Yellow crystals deposited from the water-washed phase rendered alkaline with sodium hydroxide were recovered through filtration. On the other hand, the benzene phase was dried with magnesium sulfate and benzene was distilled off. The residue thus obtained was crystallized from isopropanol and the deposited yellow crystals were recovered through filtration. The yellow crystals just mentioned above and the yellow crystals recovered through the previous filtration were joined and recrystallized from ethanol to obtain 183.3 g of yellow crystals of 1-(2,6-dichlorophenyl)-3-ethoxycarbonyl-2-quinolinoneimine. Melting point was 169°–170° C. The yield was 90% of the theoretical amount. Analytical values are shown below:

|  | Elemental analysis value (%) | | |
| --- | --- | --- | --- |
|  | C | H | N |
| Calculated | 59.84 | 3.91 | 7.75 |
| Found | 60.01 | 4.01 | 7.92 |

IR absorption spectrum (cm$^{-1}$)
NH: 3300 CO: 1700
NMR spectrum δ value (CDCl$_3$)
1.36 (3H, triplet J=7.0 Hz CH$_2$ CH$_3$) 4.35 (2H, quartet, J=7.0 Hz CH$_2$ CH$_3$) 6.78–7.68 (7H, multiplet, aromatic ring proton) 8.24 (1H, singlet, CH=C)
Mass analysis (m/e): 360 (M$^+$), 362 (M$^+_{+2}$)

EXAMPLE 2

Preparation of
1-(2,6-dichlorophenyl)-2-quinolinoneimine-3-carboxylic acid 6.75 g of 1-(2,6-dichlorophenyl)-3-ethoxycarbonyl-2-quinolinoneimine obtained in Example 1 were dissolved in 200 ml of ethanol, and 7 ml of aqueous 30% potassium hydroxide solution were added. After reacting the mixture at 70° C. for two hours and allowing it to cool, the ethanol was distilled off under reduced pressure and the residue thus obtained was shaken with chloroform and water. The aqueous phase was separated, adjusted to pH 6.0 using hydrochloric acid and agitated as it was for one hour. 5.8 g of crystals of 1-(2,6-dichlorophenyl)-

2-quinolinoneimine-3-carboxylic acid were deposited. The product had a melting point of 257.5°–259.5° C. and decomposed at that temperature. The yield was 93% of the theoretical amount. The deposited crystals of 1-(2,6-dichlorophenyl)-2-quinolinoneimine-3-carboxylic acid were recrystallized from methanol to obtain crystals having the same melting point as above. The elemental analysis values for the 1-(2,6-dichlorophenyl)-2-quinolinoneimine-3-carboxylic acid were measured after heating the crystals thereof at 100° C. for 5–6 hours. The analytical values are shown below.

|  | Elemental analysis value (%) | | |
| --- | --- | --- | --- |
|  | C | H | N |
| Calculated | 57.68 | 3.03 | 8.41 |
| Found | 57.91 | 3.08 | 8.52 |

IR absorption spectrum ($cm^{-1}$)
CO: 1645
NMR spectrum δ value ($C_2DF_3O_2$)
  6.70–8.30 (7H, multiplet, aromatic ring proton) 9.45 (1H, singlet, CH=C)
Mass analysis (m/e)
  332 ($M^+$) 334 ($M^+_{+2}$)

EXAMPLE 3

Preparation of 2-cyano-3-[2-(2,6-dichloroanilino)phenyl]acrylic acid

A mixture of 20 g of N-(2,6-dichlorophenyl)-anthranylaldehyde, 10 g of cyano-acetic acid, 17 g of acetic acid, 10 g of ammonium acetate and 100 ml of benzene was refluxed in a reaction vessel equipped with a water content removing device for two hours while removing water. After it was allowed to cool, deposited yellow crystals were recovered through filtration. The crystals, after being washed with water, were recrystallized from ethanol to obtain 5.5 g of yellow crystals of 2-cyano-3-[2-(2,6-dichloroanilino)phenyl]acrylic acid.

The product showed a melting point of 181.1°–187.8° C., at which foaming was observed, and decomposed at 198°–210° C. 11.8 g of starting material N-(2,6-dichlorophenyl)-anthranylaldehyde were recovered from the benzene phase recovered previously through filtration. The analytical values for the product thus obtained are shown below.

|  | Elemental analysis value (%) | | |
| --- | --- | --- | --- |
|  | C | H | N |
| Calculated | 57.68 | 3.03 | 8.41 |
| Found | 57.87 | 3.11 | 8.55 |

IR absorption spectrum ($cm^{-1}$)
  NH: 3340 CN: 2210
Mass analysis (m/e)
  332 ($M^+$) 334 ($M^+_{+2}$)

EXAMPLE 4

Preparation of 1-(2,6-dichlorophenyl)-2-quinolinoneimine-3-carboxylic acid 0.5 g of 2-cyano-3-[2-(2,6-dichloroanilino)phenyl]acrylic acid obtained in Example 3 were added to 20 ml of methanol and dissolved by being heated to 50° C. Then, 1 ml of an aqueous 10 N sodium hydroxide solution was added at that temperature. The mixture was allowed to cool as it was to room temperature and then agitated for 30 min. at the room temperature. Thereafter, methanol was distilled off under reduced pressure and the residue thus obtained was shaken with chloroform and water. The aqueous phase was separated, adjusted to pH 7 with hydrochloric acid and then agitated as it was for one hour. Crystals of 1-(2,6-dichlorophenyl)-2-quinolinoneimine-3-carboxylic acid were deposited. Respective analytical values for the products coincided with those of the products obtained in Example 2.

EXAMPLE 5

The pharmacological effects of the compound of the formula (I) according to this invention are shown below in comparison with commercial pharmaceuticals as references. The commercial pharmaceuticals used as the reference were INDOMETHACIN (referred to as IM hereinafter), DICLOFENAC SODIUM (referred to as DF hereinafter), PHENYLBUTAZONE (referred to as PB hereinafter), and MEFENAMIC ACID (referred to as MA hereinafter).

(1) Carageenin-Induced Edema in foot

According to the method of C. A. Winter reported in Proceedings of the Society for Experimental Biology and Medicine, vol. 111, p 544 (1962) and using rats (male wister-strain, about 150 g body weight), the compound was applied through oral administration in 1% carboxymethylcellulose suspension. For the control group, 1% carboxymethylcellulose solution was applied in the same manner through oral administration.

Inhibition ratio (%) = (A − B)/A × 100, wherein A is the volume increase in foot (%) for the control group, B is the volume increase in foot (%) for the group treated with the compound.

Figure 2:
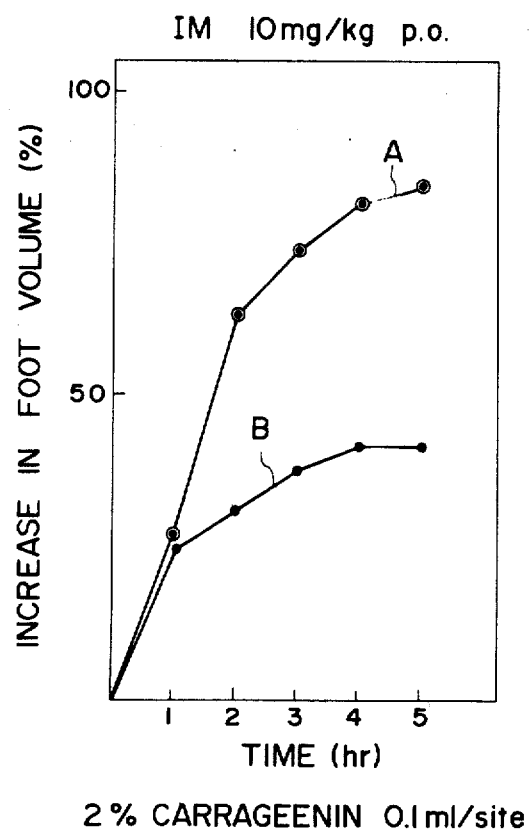
FIG. 2 is a graph showing the result of an edema test using a commercial pharmaceutical, INDOMETHACIN (IM)
Figure 3:
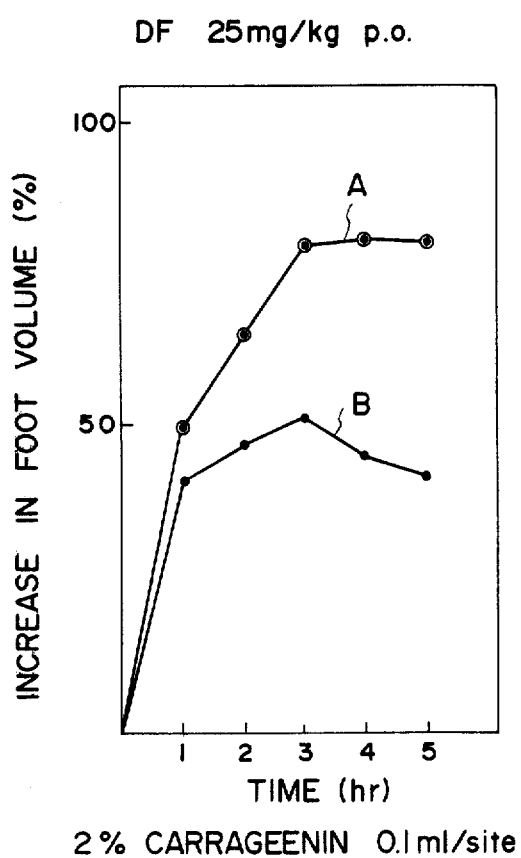
FIG. 3 is a graph showing the result of an edema test using another commercial pharmaceutical DICLOFENAC SODIUM (DF).

The results are shown in FIG. 1, FIG. 2 and FIG. 3.

(2) Granuloma Assay

According to the method of Fujinawa, et al reported in Pharmacometrics, vol. 16, p 353 and using rats (male Wister-strain, about 160 g body weight), the compound was applied in 1% carboxymethylcellulose suspension through oral administration by 10 mg/kg for 6 successive days. For the control group, 1% carboxymethylcellulose solution was applied in the same manner through oral administration. Dry weight of granuloma was measured for the judgement.

Inhibition ratio (%) = (E − F)/E × 100, wherein E is dry weight (mg) in the control group, F is dry weight (mg) in the test group treated with the compound.

| Compound | Dosage (mg/kg p.o.) | Dry weight (mg) | Inhibition ratio (%) |
| --- | --- | --- | --- |
| Compound of the formula (I) according to this invention | 10 | 22.0 ± 4.0 | 33.1 |
| DF | 10 | 18.2 ± 1.7 | 44.7 |
| IM | 10 | 16.4 ± 1.8 | 50.2 |
| Control | — | 36.5 ± 2.6 | — |

(3) Acetic Acid Writhing Test

According to the method of B. A. Whittle reported in British Journal of Pharmacology, vol. 22, p 246 (1964) and using mice (male ddN-strain, about 18 g body weight), the compound was applied through oral administration in 1% carboxymethylcellulose suspension and, 30 minutes afterwards, 0.7% acetic acid was applied through intra-peritoneal injection by 0.1 ml/10 g. The counts of stretching (squirming reaction) appearing for 20 minutes after the injection of acetic acid were measured. For the control group, 1% carboxymethylcellulose solution was used.

Inhibition ratio (%) = $(I-J)/I \times 100$, wherein I is the counts of stretching in the control group, J is the counts of stretching in the test group applied with the compound

| Compound | Dosage (mg/kg. p.o.) | Inhibition ratio (%) |
|---|---|---|
| Compound of the formula (I) according to this invention | 5 | 5.0 |
|  | 10 | 40.0 |
|  | 50 | 91.4 |
| DF | 5 | 20.3 |
|  | 10 | 34.0 |
|  | 50 | 49.4 |
| PB | 10 | — |
|  | 50 | 9.2 |
| MA | 25 | — |
|  | 50 | 14.3 |
| IM | 5 | — |
|  | 10 | 45.6 |
|  | 25 | — |
| Control | — | — |

As shown in the foregoing, the compound of the formula (I) according to this invention exhibits anti-inflammatory effects comparable with those of commercial products and analgesic effects superior to those of commercial products. Further, the compound was of low toxicity, having an $LD_{50}$ value of 648.2 (523.9–732.0) mg/kg P.O. (male ddN-strain mouse)

Industrial Applicability

The compound of the formula (I) according to this invention is excellent in anti-inflammatory effects and analgesic effects, and the composition containing the compound is useful as an anti-inflammatory and analgesic agent.

I claim:

1. 1-(2,6-dichlorophenyl)-2-quinolinoneimine-3-carboxylic acid represented by the formula (I):

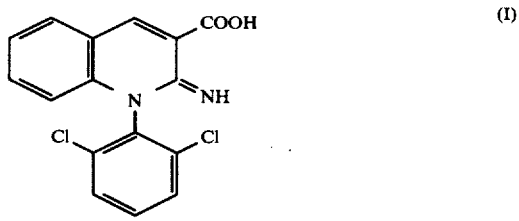

and pharmacologically acceptable salts thereof.

2. An anti-inflammatory and analgesic composition wherein a pharmaceutically effective amount of 1-(2,6-dichlorophenyl)-2-quinolinoneimine-3-carboxylic acid represented by the formula (I):

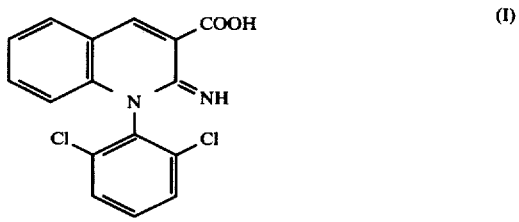

or a pharmaceutically acceptable salt thereof is contained as an effective ingredient.

* * * * *